United States Patent
Boese et al.

(10) Patent No.: US 7,421,061 B2
(45) Date of Patent: Sep. 2, 2008

(54) METHOD AND MEDICAL IMAGING SYSTEM FOR COMPENSATING FOR PATIENT MOTION

(75) Inventors: Jan Boese, Eckental (DE); Norbert Rahn, Forchheim (DE)

(73) Assignee: Siemens Aktiengesellschaft, Munich (DE)

( * ) Notice: Subject to any disclaimer, the term of this patent is extended or adjusted under 35 U.S.C. 154(b) by 430 days.

(21) Appl. No.: 11/045,721

(22) Filed: Jan. 28, 2005

(65) Prior Publication Data
US 2005/0171420 A1 Aug. 4, 2005

(30) Foreign Application Priority Data
Jan. 29, 2004 (DE) .................. 10 2004 004 604

(51) Int. Cl.
*H05G 1/60* (2006.01)
*H05G 1/64* (2006.01)

(52) U.S. Cl. .................. 378/98.12; 378/95; 378/205
(58) Field of Classification Search .......... 378/95, 378/98.12, 205
See application file for complete search history.

(56) References Cited

U.S. PATENT DOCUMENTS

| | | | |
|---|---|---|---|
| 4,870,692 A | | 9/1989 | Zuiderveld et al. |
| 5,023,894 A | * | 6/1991 | Yamashita et al. ............. 378/4 |
| 5,081,984 A | | 1/1992 | Wess et al. |
| 5,848,121 A | * | 12/1998 | Gupta et al. ................... 378/62 |
| 6,491,429 B1 | * | 12/2002 | Suhm ........................ 378/205 |
| 6,561,695 B2 | * | 5/2003 | Proksa ....................... 378/207 |
| 6,584,174 B2 | * | 6/2003 | Schubert et al. ............. 378/165 |
| 6,842,502 B2 | * | 1/2005 | Jaffray et al. ................. 378/65 |
| 2002/0085668 A1 | | 7/2002 | Blumhofer et al. |
| 2003/0083562 A1 | | 5/2003 | Bani-Hashemi et al. |
| 2006/0023840 A1 | * | 2/2006 | Boese ...................... 378/98.12 |
| 2007/0003014 A1 | * | 1/2007 | Boese et al. .................. 378/95 |

OTHER PUBLICATIONS

Erik H. W. Meijering et al., "Reduction of Patient Motion Artifacts in Digital Subtraction Angiography: Evaluation of a Fast and Fully Automatic Technique", Radiology, Apr. 2001, pp. 288-293, vol. 219, No. 1.

(Continued)

*Primary Examiner*—Edward J. Glick
*Assistant Examiner*—Thomas R Artman

(57) ABSTRACT

The present invention relates to a method and also an imaging system to compensate for patient motion when recording a series of images in medical imaging, in which a number of images of an area under examination of a patient (17) are recorded at intervals with an imaging system (1) and are related to one another. With the method a localization system (2) is used as the series of images are being recorded to permanently or at a time close to the recording of the individual images, record a momentary spatial location of the area under examination in a reference system permanently linked to the imaging system (1), a first spatial location of the area under examination recorded close to the time of recording of a first image is stored, and a deviation of the images recorded momentarily in each case of the first spatial location is determined and by changing the geometrical circumstances of the imaging system (1) at a time to close the recording of the spatial location and/or through geometrical adaptation of an image content of an image just recorded, is at least approximately commentated for, so that the images show the area under examination in the same position and orientation. The method does not require any time-consuming interaction with the operator and is also suitable for compensating for larger movements of the patient.

19 Claims, 2 Drawing Sheets

OTHER PUBLICATIONS

M. Hemmendorff et al., "Motion Compensated Digital Subtraction Angiography", SPIE Conference on Image Processing, San Diego USA, Feb. 1999, pp. 1396-1405, vol. 3661.

Erik H. W. Meijering et al., "Retrospective Motion Correction in Digital Subtraction Angiography: A Review", IEEE Transactions on Medical Imaging, Jan. 1999, pp. 2-37, vol. 18, No. 1.

* cited by examiner

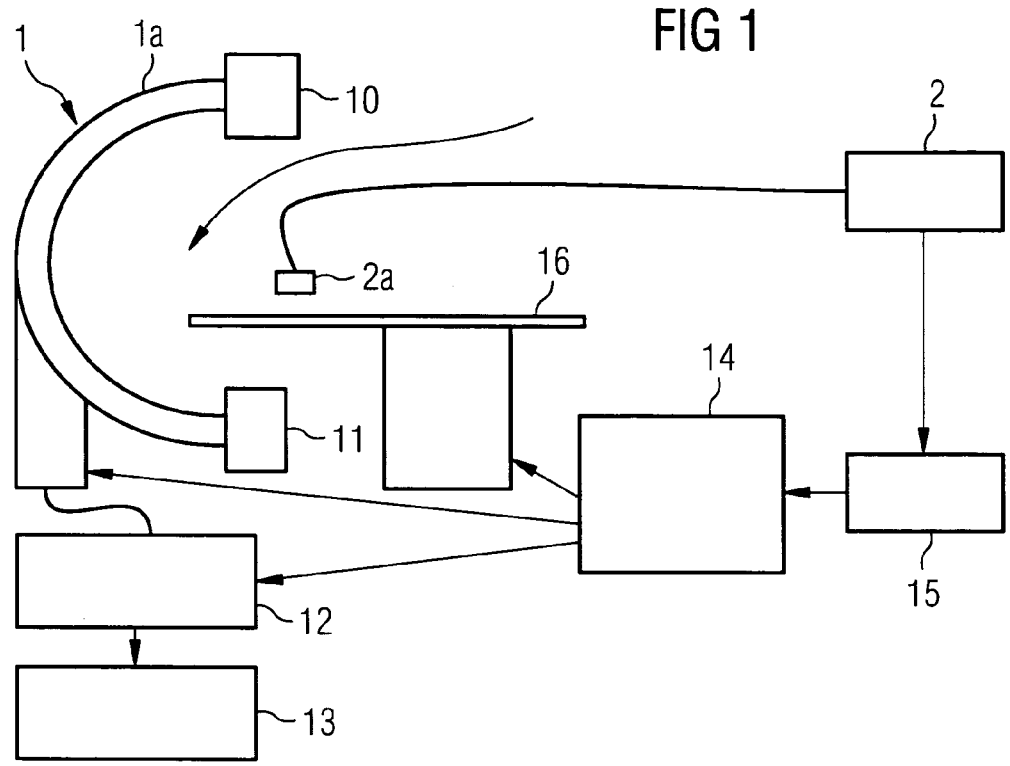
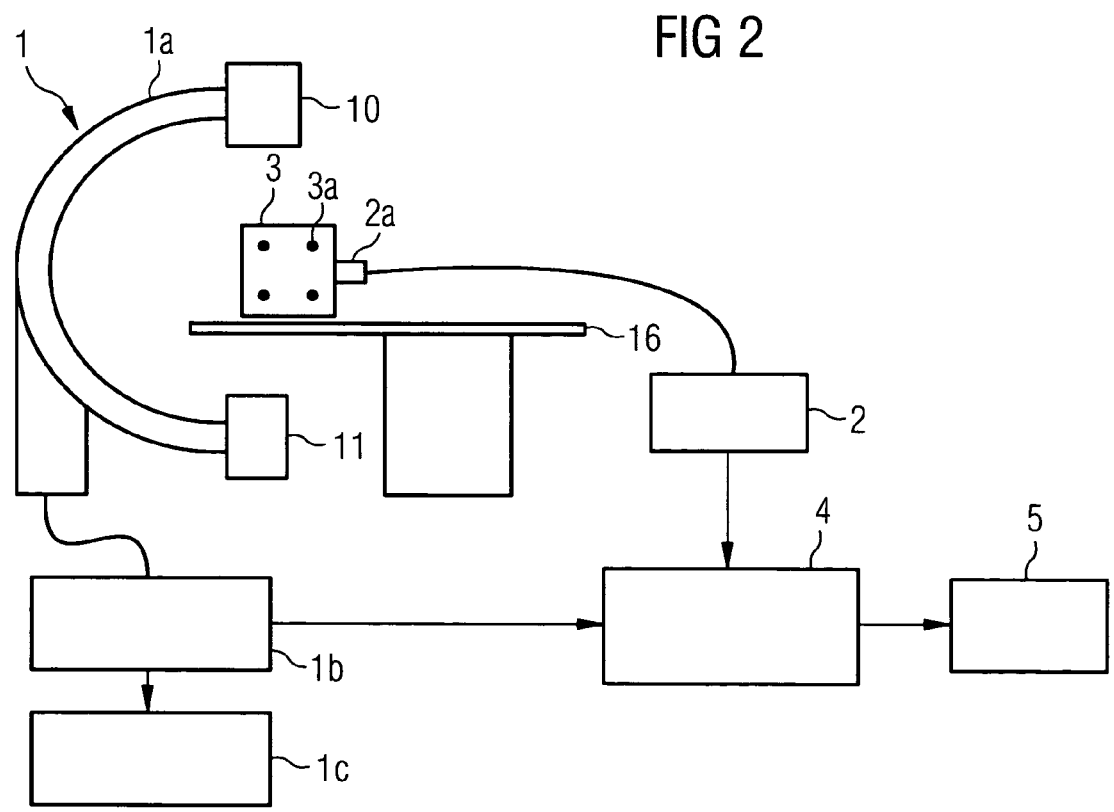

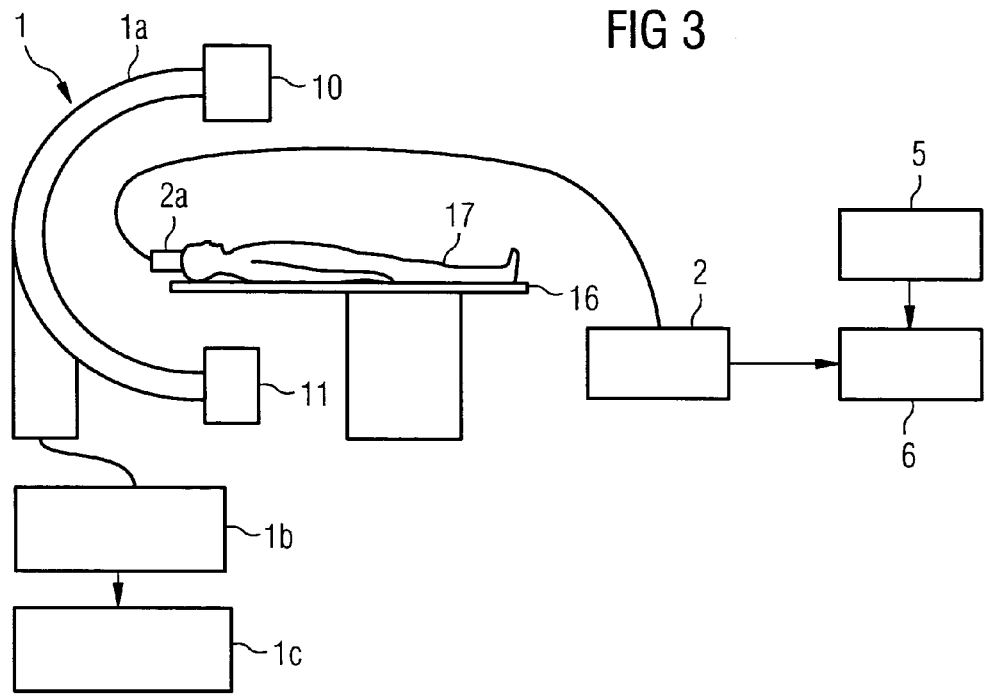
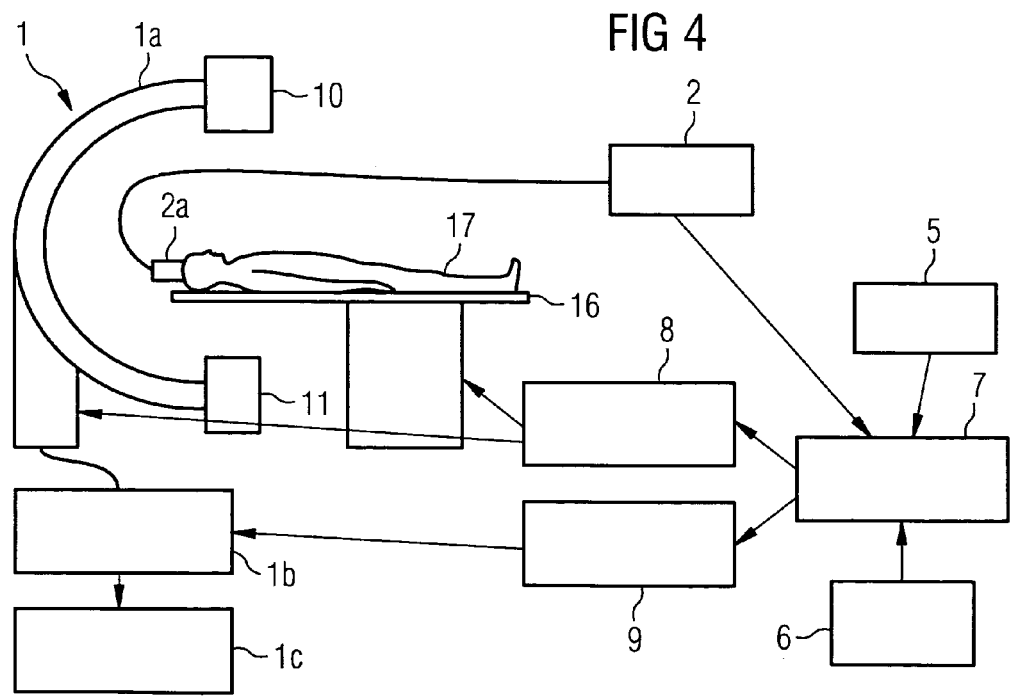

METHOD AND MEDICAL IMAGING SYSTEM FOR COMPENSATING FOR PATIENT MOTION

CROSS REFERENCE TO RELATED APPLICATIONS

This application claims priority to the German application No. 10 2004 004 604.2, filed Jan. 29, 2004 which is incorporated by reference herein in its entirety.

FIELD OF INVENTION

The present invention relates to a method to compensate for patient movements when recording a series of medical images in which a number of images of an area under examination of the patient are taken at intervals with an imaging system and are compared to one another, as is the case for example in Digital Subtraction Angiography (DSA) or roadmapping. The invention further relates to a medical imaging system with radiation source, detector, patient support, image processing unit and image display unit which is embodied to execute the method.

BACKGROUND OF INVENTION

In a main area of application of the present method, the area of digital subtraction angiography, blood vessels of the human body are recorded with an imaging system, in this case an X-ray system, and displayed. With this method series of X-ray images of the area under examination of interest for the patient are recorded while a contrast means is injected to highlight the vessels (filling images). Furthermore an image of the area under investigation is recorded without injecting a contrast means (mask image). By digitally subtracting the mask image from the relevant filling images, subtraction images are obtained on which only the vessels are visible while overlays from other X-ray-absorbing structures, such as for example bones, disappear because of the subtraction.

The subtraction of the images however requires these images to be recorded under the same geometrical conditions so that they cover the same area. As a result of motion of the recorded structures between the individual recordings the result can be disruptive motion artifacts in the subtracted images. These can be caused by the patient moving between the recording of the mask image and the recordings of the filling images. A consequence of these movements can be that the resulting subtraction image can no longer be used for the diagnosis. Thus it can occur in practice that, because of these types of motion artifacts, disrupted subtraction images have to be repeated. This often involves additional effort in time and contrast means as well as exposing the patient to additional radiation.

A method known as roadmapping is a technique associated with digital subtraction angiography. This technique is applied for selective categorization of vessels in interventional therapy. With such vessels the current position of an X-ray-absorbing catheter is shown by X-ray fluoroscopy in a two-dimensional image. To also enable the blood vessel to be recognized as what is known as a roadmap an image is recorded at the start of the intervention for which a small amount of contrast means has been injected. This image is retained as a mask image. The following fluoroscopy images obtained without injection of a contrast means are subtracted from the mask image in each case. In this way subtraction images are obtained on which the catheter is visible as a bright object against the dark blood vessel and the background has been eliminated by subtraction.

Like digital subtraction angiography, roadmapping is also disrupted in the same way by motion of the imaged structures during recording of a series of images. For motion between the recording of the mask image and the relevant fluoroscopy image two problems arise here however. One is that the background is no longer correctly subtracted so that image artifacts occur. The other is that it can occur that the position determined by the image of the catheter relative to the blood vessel shown is not correct. This serious error can for example result in the image showing a catheter outside the vessel although it is actually located inside the vessel. In an extreme case such incorrect representations can lead to errors in catheter control and result in injuries to the vessel. If the patient moves during the intervention it is therefore frequently necessary for the roadmap to be refreshed by recording a new mask image. This requires additional time and uses up more contrast means and is associated with a higher dose of radiation for the patient.

Different solutions are currently known for avoiding or for reducing this problem. The following three types of approach to solutions can thus be identified.

Patient-linked solutions aim to avoid movement of the patient during image recording. Thus for example, during thorax examinations, the patient can be trained to hold their breath while the series of images is being recorded. A further option is to avoid a number of sources of motion artifacts by full anesthetic. A disadvantage of patient-linked methods lies in the fact that they are only partly effective or can-not always be used. A full anesthetic for example involves many risks and is thus not medically advised for many applications of digital subtraction angiography. In addition, even with a full anesthetic, a number of sources of motion artifacts, such as breath movement, are still present.

For the solutions which are linked to how the images are recorded the image recording is executed so that motion artifacts are minimized. Previously the main method known in this area has been the Gating method in which the recording is coupled with a physiological measurement. Thus for example with ECG Gating images of only acquired in a particular heart phase, to compensate for heart movements. Gating methods are however only usable for a few specific applications and can only avoid motion artifacts caused by specific sources for which physiological signals can be measured.

A further approach to a solution for avoiding motion artifacts consists of retrospective image processing of the recorded images. With these techniques the aim is to use image processing to obtain a better match between mask image and filling image. The simplest technique used is known as pixel shifting or subpixel shifting, in which the user shifts the mask image in relation to the filling image manually in two dimensions until a minimization of the motion artifacts is obtained in the subtraction image. This method is implemented in all commercial angiography systems. Automatic methods which define the best match on the basis of quantifiable similarity measures are present in a few commercial angiography systems. More complex methods do not use global pixel shifting over the entire area of the image but optimize local areas of the image separately from one another, as described for example in U.S. Pat. No. 4,870,692 A. Furthermore scientific literature proposes numerous more expensive methods for movement correction. These essentially involve optimization methods in which attempts are made to find the transformation between masking image and a filling image which results in the fewest motion artifacts. Further examples of retrospective image processing can be found in the publications "Motion compensated digital subtraction angiography", M. Hemmendorff et al., SPIE '99, San Diego USA, Proceedings of play International Symposium on Medical Imaging 1999, Volume 3661, Image Processing, February 1999; Meijering E. H. et al., "Reduction of patient motion artifacts in digital subtraction angiography: evaluation of a fast and fully automatic technique", Radiology, 2001 April; 219(1): 288-293; or "Retrospective Motion Correction in Digital Subtraction Angiography: A Review", Erik H. W. Meijering et al., IEEE Transactions on Medical Imaging, Vol. 18, No. 1, January 1999, pp. 2-21.

SUMMARY OF INVENTION

Retrospective image processing can however only approximately compensate for motion. Not all motion can be corrected. Even when the method is restricted to a correction of 6 degrees of freedom corresponding to the rotation and translation of a rigid body the motion cannot be uniquely determined from the two-dimensional images. Furthermore the complicated image processing methods demand extensive processing power and are thus difficult to implement in real time. Manual methods for image processing (pixel shifting) need user interaction and can demand significant amounts of time. They can also basi-cally only be used for retrospective improvement of recorded DSA images since with roadmapping there is barely time for interaction.

Using this prior art as a starting point, an object of the present invention is to specify a method as well as an associated imaging system to compensate for the motion of patients when recording a series of images in medical imaging, with which the motion of the patient can be compensated for while the images are being recorded without time-consuming user interaction, with the method being able to be implemented in real time. The method and the associated imaging system should in particular improve image results in a digital subtraction angiography and roadmapping with the lowest possible outlay as regards the operator's time.

The object is achieved by the claims. Advantageous embodiments of the method and of the arrangement are the subject of dependent claims or can be taken from the subsequent description as well as the exemplary embodiments.

In the present method for compensating for patient motion when recording a series of images in medical imaging, in which a number of images of the area under examination of a patient are recorded at intervals with an imaging system and are related to one another, a localization system records a current spatial location of the area under investigation in a reference system connected to the imaging system continuously or at least close to the time at which the individual images are recorded in each case. A first spatial location of the area under examination recorded close to the point of recording of a first image is retained and deviations of the relevant recorded momentary images from first spatial location determined and by changing geometrical circumstances of the imaging system close to the time of recording the spatial location, preferably in real time and/or by geometrical adaptation of an image just recorded in each case are at least approximately compensated for so that the images show the area under examination in the same position and orientation in each case.

The method can be used especially for motion compensation in digital subtraction angiography or with roadmapping to obtain individual images for subtraction which cover as much of the same area as possible. Therefore even while the images are being recorded the method compensates for patient motion or motion of the visible area of the patient under examination by a control, preferably a real-time control of the geometrical circumstances of the imaging system, where necessary in combination with geometrical adaptation of the image content. This involves controlling at the current spatial location of the patient or of the area under examination, that is both the current position and also the current orientation detected by a localization system, and then controlling the geometrical parameters of the imaging system so that the relative relationship between the area under examination for which the image is to be recorded and the recording system remains constant. Individual degrees of freedom can be compensated for in this case by adaptation, especially rotation or translation, of the image content of the recorded image.

A device with which the position and orientation (a total of six degrees of freedom) of a position sensor in the three-dimensional area can be measured is preferably used as a localization system. Examples of these types of localization system are optoelectronic position sensors, for example OPT-TRAK 3020 from Northern Digital, Waterloo, Canada, channel or electromagnetic localization systems such as those from Biosense Webster Inc., Diamond Bar, Calif., USA or the Bird sys-tem from Ascension, Milton, Vt., USA. Naturally other localization systems allowing recording of the spatial location of the area under examination within the space can be used. Thus for example 3 position sensors can also be applied to an object under examination, from the spatial location of which the orientation of the examination area can also be derived. Optical scanning systems or similar, which operate without attaching sensors to the patient, are also possible.

The present method, by contrast with most previously known methods of motion correction, manages without interaction with the operator. The proposed method only requires a position sensor to be accommodated on the patient where necessary. Consequently no further user interaction is required for motion compensation. The principle of previous methods for retrospective image processing dictates that they only operate approximately. It is barely possible to correct large movements using these methods, and small movements can only be approximately corrected. The proposed method operates with high precision even for large movements, so that the need to record a mask image more than once is avoided. The saves time, contrast means and reduces the applied X-ray dose in the case of X-ray image recording. The present method also makes it possible in particular cases to dispense with sedating or anesthetizing the patient merely for the purpose of minimizing motion artifacts.

Different components of the imaging system can be included to compensate for deviations resulting from patient movement by adapting the geometrical circumstances of the imaging system. This adaptation is preferably undertaken by a translation and/or rotation of the patient table in 1-3 degrees of freedom. The patient table is already movable with C-arm de-vices for angiography applications by motor at least in the 3 degrees of translation freedom.

Furthermore the deviations can be matched by a rotation of the C-arm in RAO/LAO or cranio/caudal direction in 2 degrees of freedom. In a further embodiment a detector is used which can be rotated in 1-3 degrees of freedom, so that deviations can also be compensated for by moving the detector.

To compensate for the detected deviations it is further possible to geometrically modify the image content of the recorded images. This relates in particular to a rotation of the image content at right angles to the image plane as well as to the translation in the two degrees of translation freedom of the two-dimensional recorded image. Furthermore scaling of the image is possible. Depending on the type of patient motion a combination of the two compensation techniques can also be advantageous, i.e. the modification of the geo-metrical circumstances of the imaging system and the geometrical adaptation of the image content.

Naturally, with the present method, after the at least approximate compensation of the movement, retrospective image processing methods can also be used in order to further improve the image results. The approximate compensation by modifying the geometrical circumstances of the imaging system can be used in this case to compensate for rough movements, while remaining small errors can be rectified by retrospective image processing.

The present imaging system comprises at least a radiation source and a detector, a patient support, a control unit, an image processing unit and an image display unit. The geometrical circumstances for imaging can be modified by motor-driven movement of the patient support as well as the imaging unit, consisting of radiation source and detector opposite it. The outstanding feature of the imaging system is that a compensation unit is provided, which controls in real-time one or more of the components that can be modified in real time to change the geometrical circumstances of the imaging system and/or the image processing unit for geometrical adaptation of an image content of an image just recorded in each case so that the movements of a patient recorded by a localization system are at least approximately compensated for. The imaging system here is preferably embodied in the form of a C-arm device, with the positions of the patient table and of the C arm being able to be altered as movable components.

BRIEF DESCRIPTION OF THE DRAWINGS

The present method as well as the associated device are explained in more detail again below with reference to an exemplary embodiment in connection with the drawings. The Figures show:

FIG. 1 an example for a C-arm device as an imaging system for executing the present method;

FIG. 2 an example for calibrating the localization system in the C-arm device of FIG. 1;

FIG. 3 an example for recording the first image with the first spatial location of the area under examination; and FIG. 4 an example for recording the further images as well as motion compensation.

DETAILED DESCRIPTION OF INVENTION

The present method is described below with reference to an X-ray angiography system for applications in neuroradiology. The method can naturally also be used in other fields in which digital subtraction angiography and/or roadmapping are employed. The present method can also be used with other medical imaging techniques involving having to record a series of images and relate them to one another.

The embodiments below are typically restricted to the case of correcting the patient's head movements. Since the head can be approximately regarded as a rigid body, the motion can be restricted to the 6 degrees of freedom of the translation and rotation of a rigid body in three-dimensional space.

An X-ray angiography system 1 for neuro-radiology, which is shown schematically in FIG. 1, is used to record the images. The X-ray angiography system 1 includes a C-arm 1a which can be rotated around two axes, to which an X-ray tube 10 and a detector 11 arranged opposite the X-ray tube are attached, an image processing unit 12 and an image display unit 13. Furthermore this system includes the motor-driven adjust-able patient table 16, a control unit 14 for image recording control as well as the compensation unit 15. Rotation of the C-arm 1a allows different projections of the area under examination of the patient supported on the patient table 16 to be recorded as two-dimensional images. With the present method a localization system 2 is used to record the location of the area of the patient under examination, in the present example the patient's head. This localization system 2 in the present example is a device with which the position and orientation of a position sensor 2a can be measured in the three-dimensional space.

Before the localization system 2 is used, a calibration is performed between the coordinate systems of the angiography system 1 and the localization system 2. The calibration consists of 6 parameters which describe the rotation and translation of the two coordinate systems relative to one another. Different methods are available for this type of calibration:

One option for calibration consists of using a calibration phantom 3, which is recorded by means of X-ray imaging from different angles, as is illustrated in FIG. 2. During image recording 1b the sensor 2a of the localization system 2 is connected to the calibration phantom 3. The fixed rela-tion-ships of markings 3a on the phantom 3 which can be de-tected on the recorded X-ray images and the sensor 2a, al-lows the spatial location of the sensor 2a (and thereby of the coordinate system of the localization system) relative to the coordinate system of the angiography system 1 to be calculated in a step 4. These relationships or calibration data are stored (5).

A further calibration technique relates to calibration of an electromagnetic localization system. Here the transmitter could be accommodated at a point for which the position relative to the coordinate system of the angiography unit is known. In this case no further steps are necessary for the calibration.

For use of an optical localization system a marker plate could be mounted on the detector or another part of the angiography unit, for which the position is known relative to the coordinate system of the angiography unit. Here too no further calibration steps are then required. A further option without additional calibration steps consists in this case of installing the camera of the optical localization system permanently on the ceiling of the examination room.

The calibration which is undertaken in the present example with the first technique described is required as a rule only once on installation of the system.

The procedure for executing the present method can be seen from FIGS. 3 and 4. First the sensor 2a of the localization system 2 is fixed to the head of the patient 17, as can be seen schematically from FIG. 3. This can be done for example by an adhesive connection. At the beginning of the series of recordings, for example of DSA or roadmap recordings, on recording 1b of the mask image, the current spatial location of the sensor 2a and thus of the head of the patient 17 is recorded automatically with the localization system 2, i.e. without user interaction. This starting location, i.e. position and orientation, is calculated taking into account the stored calibration data 5 in the reference system of the imaging device and the original position and—orientation are stored (6).

During the subsequent image recording 1b the location of the sensor 2a will be determined. In the combination unit 15 the current location is compared to the stored initial location 6 and the change in the patient's location is determined (step 7) from the stored calibration data 5 and the stored initial location 6. This information is transmitted to the control 14 of the angiography system 1. The control 14 adapts the recording geometry 8 by controlling the drive for the patient table 16 as well as the drive for the C-arm 1a and if nec. by controlling the image processing unit 9 such that patient motion can be compensated for.

Subsequently the mask image and the relevant filing images or fluoroscopy images can be subtracted from one another in the image processing unit 12 and the subtraction images obtained displayed on the image display unit 13 (1c).

In principle the 6 degrees of freedom of patient movement could be completely compensated for by a corresponding adjustment of the patient table 16 in 6 degrees of freedom. However other options could also be better for executing the method. Thus, for a typical neuro-angiography system, the following parameters might typically be adapted:

Adapting the translation of the patient table in 3 degrees of freedom;

Adapting the rotation of the C-arm in two directions (2 degrees of freedom); and Rotation of the image content of the recorded image (1 degree of freedom).

After the end of recording of the series of images the stored initial position or location is discarded the process continues for recording a new series of images with the recording of a new initial location.

The invention claimed is:

1. A method of compensating for patient motion when recording a series of medical images consisting of 2D medical images, wherein the medical images consisting of 2D medical images of an examination area of a patient are recorded at specific time intervals using an imaging system and are correlated with each other, and a current spatial position of the examination area is determined relative to a frame of reference assigned to the imaging system, by a localization system, the method comprising:

determining a first spatial position of the examination area substantially in parallel with recording a first medical image consisting of 2D medical image of the series;

recording farther medical images consisting of 2D medical images of the series;

continuously determining the current spatial position of the examination area for each current recorded further medical image consisting of 2D medical image, by the localization system while recording the series of medical images consisting of 2D medical images;

determining a difference between each current and the first spatial positions based on the each current recorded farther medical image consisting of 2D medical image and the first medical image consisting of 2D medical image; and compensating the difference on the each current recorded further medical image consisting of 2D medical image by adjusting the imaging system such that the first and further medical images consisting of 2D medical images show the examination area in the same position and orientation.

2. The method according to claim 1, wherein adjusting the imaging system includes adjusting at least one geometrical proportion of the imaging system.

3. The method according to claim 2, wherein adjusting the geometrical portion includes a translation of a patient table of the imaging system.

4. The method according to claim 2, wherein adjusting the geometrical portion includes a rotation of a patient table of the imaging system.

5. The method according to claims 2, wherein adjusting the geometrical portion includes a rotation of an image recording detector.

6. The method according to claims 2, wherein the imaging system includes a C-arm device and adjusting the geometrical portion includes a rotation of the C-arm.

7. The method according to claim 1, wherein adjusting the imaging system includes processing at least one of the further medical images with regard to adjusting at least one geometrical proportion of an image content of the further medical images.

8. The method according to claims 7, wherein processing at least one of the further medical images includes a translation of the image content.

9. The method according to claims 7, wherein processing at least one of the further medical images includes a scaling of the image content.

10. The method according to claim 1, wherein the method includes a digital subtraction angiography or a pathfinding technique.

11. The method according to claim 10, wherein the pathfinding technique includes roadmapping.

12. The method according to claim 1, wherein the current spatial position of the examination area is determined continuously while the series is recorded.

13. The method according to claim 1, wherein the current spatial position of the examination area is determined substantially in parallel with recording an individual image of the series.

14. The method according to claim 1, wherein the localization system comprises at least one sensor attached to the patient.

15. The method according to claim 1, wherein a remaining difference between the current and the first spatial positions is compensated for by applying a retrospective image processing method to the recorded medical images.

16. An imaging system, comprising:

at least one radiation source;

a radiation detector that records a series of medical images of an examination area of a patient;

a patient table adjustable by a motor operatively connected to the patient table;

a localization system for detecting patient motion;

an image processing unit for processing the recorded image;

a control unit for controlling the radiation source, the radiation detector, the patient table and the image processing unit;

an image display unit, wherein the radiation source, the radiation detector and the patient table are adjustable components and the mutual positioning of which relative to each other defines the geometrical proportions of the imaging system; and a compensation unit for adjusting the imaging system in real time using the control unit such that the motion of the patient recorded by the localization system is compensated for, wherein the compensation unit is configured to:

determine a first spatial position of the examination area substantially in parallel with recording a first medical image consisting of 2D medical image of the series;

continuously determine a current spatial position of the examination area for each current recorded further medical image consisting of 2D medical image, by the localization system while recording the further medical images of the series consisting of 2D medical images;

determine a difference between each current and the first spatial positions based on the each current recorded farther medical image consisting of 2D medical image and the first medical image consisting of 2D medical image; and compensate the difference on the each current recorded further medical image consisting of 2D medical image by adjusting the imaging system such that the first and further medical images consisting of 2D medical images show the examination area in the same position and orientation.

17. The imaging system according to claim 16, wherein adjusting the imaging system includes activating at least one of the adjustable components for adjusting at least one geometrical proportion of the imaging system.

18. The imaging system according to claim 16, wherein adjusting the imaging system includes activating the imaging processing unit for processing at least one recorded medical image with regard to adjusting at least one geometrical proportion of an image content of the recorded medical image.

19. The imaging system according to claim 16, wherein the imaging system is an X-ray system having a C-arm device.

* * * * *